(12) United States Patent
Zhou et al.

(10) Patent No.: US 7,687,549 B2
(45) Date of Patent: Mar. 30, 2010

(54) CARBOXYLIC ACID COMPOUNDS AND POLYESTER OLIGOMERS AND POLYMERS MADE THEREFROM

(75) Inventors: Shuang Zhou, Oskaloosa, IA (US); Tzyy-Jan Han, Pella, IA (US)

(73) Assignee: Cargill, Incorporated, Wayzata, MN (US)

(*) Notice: Subject to any disclaimer, the term of this patent is extended or adjusted under 35 U.S.C. 154(b) by 361 days.

(21) Appl. No.: 11/629,745

(22) PCT Filed: Jun. 30, 2005

(86) PCT No.: PCT/US2005/023741

§ 371 (c)(1),
(2), (4) Date: Aug. 13, 2007

(87) PCT Pub. No.: WO2006/007591

PCT Pub. Date: Jan. 19, 2006

(65) Prior Publication Data

US 2008/0146690 A1 Jun. 19, 2008

Related U.S. Application Data

(60) Provisional application No. 60/584,664, filed on Jul. 1, 2004.

(51) Int. Cl.
- C07C 69/67 (2006.01)
- C08G 63/60 (2006.01)
- C09D 167/06 (2006.01)
- C08F 2/50 (2006.01)

(52) U.S. Cl. .............. 522/41; 522/44; 522/46; 522/107; 522/179; 528/296; 528/306; 526/304; 560/180; 560/181; 560/190

(58) Field of Classification Search ............... 522/41, 522/44, 46, 107, 179; 526/318.2, 321, 319, 526/304, 217.1; 560/176, 180, 181, 190, 560/205, 220, 221, 222, 64, 66, 76, 146, 560/142; 528/296, 306

See application file for complete search history.

(56) References Cited

U.S. PATENT DOCUMENTS

| | | | |
|---|---|---|---|
| 3,222,421 A | 12/1965 | Lundberg | |
| 3,979,393 A | 9/1976 | Kvita et al. | |
| 4,157,418 A | 6/1979 | Heilmann | |
| 4,320,173 A | 3/1982 | Coran et al. | |
| 5,369,142 A | 11/1994 | Culbertson et al. | |
| 5,863,998 A | 1/1999 | Cai | |
| 6,107,428 A | 8/2000 | Yamaguchi et al. | |
| 6,153,788 A * | 11/2000 | Fischer et al. | 560/224 |

FOREIGN PATENT DOCUMENTS

| GB | 1 360 688 | 7/1974 |
|---|---|---|
| JP | 09 176 146 | 7/1997 |

OTHER PUBLICATIONS

Cunliffe et al., "The Inhibition of Glutamate Dehydrogenase by Derivatives of Isophthalic Acid," *Phytochemistry* 22(6):1357-1360, 1983.

Ezhova et al., "Acylation of Aminoaromatic Carboxylic Acids by Methacrylyl Chloride," *Bulletin of the Academy of Sciences of the USSR, Division of Chemical Science* 29(2):267-269, 1980.

Hayakawa et al., "Efficacy of self-etching primers containing carboxylic acid monomers on the adhesion between composite resin and dentin," *Journal of Oral Science* 40(1):9-16, 1998.

Kalgutkar et al., "Design, Synthesis, and Biochemical Evaluation of N-Substituted Maleimides as Inhibitors of Prostaglandin Endoperoxide Synthases," *J. Med. Chem.* 39:1692-1703, 1996.

International Search Report for PCT/US2005/023741.

* cited by examiner

*Primary Examiner*—Susan W Berman

(57) ABSTRACT

The invention relates to di- and tri-carboxylic acid compounds and polyester oligomers and polymers made therefrom. Curable compositions comprising the polyester oligomers and polymers are also described.

20 Claims, No Drawings

US 7,687,549 B2

CARBOXYLIC ACID COMPOUNDS AND POLYESTER OLIGOMERS AND POLYMERS MADE THEREFROM

PRIORITY CLAIM

This is the § 371 U.S. National Stage of International Application No. PCT/US2005/023741, filed Jun. 30, 2005, which was published in English under PCT Article 21(2), which claims the benefit of U.S. Provisional Patent Application No. 60/584,664 filed Jul. 1, 2004, which is incorporated herein by reference in its entirety.

FIELD OF THE INVENTION

The invention relates to di- and tri-carboxylic acid compounds and polyester oligomers and polymers made therefrom. The invention also includes curable compositions comprising the polyester oligomers and polyester polymers.

SUMMARY OF THE INVENTION

The invention relates to di- and tri-carboxylic acid compounds and polyester oligomers and polymers made therefrom.

In one aspect, the invention provides di- and tri-functional compounds that may be represented by formula (A):

HOOC—Y—COOH   (A)

where:
—Y— is selected from the group consisting of:

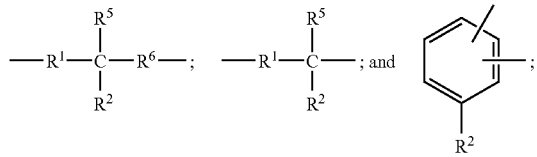

—$R^1$— is a divalent aliphatic organic group;
—$R^2$ is —X—C(=O)—$R^3$—C(=O)OH or —X—C(=O)—$R^4$;
—X— is —O— or —NH—;
—$R^3$— is a divalent organic group having at least one carbon-carbon double bond;
—$R^4$ is a monovalent organic group having at least one carbon-carbon double bond;
—$R^5$ is hydrogen or an alkyl group; and
—$R^6$— is a divalent aliphatic organic group.

The compounds may be used to prepare polyester oligomers and polyester polymers. In some embodiments, the polyester oligomers and polymers have improved properties.

In another aspect, the invention provides a composition of matter comprising a polyester oligomer or polyester polymer comprising the reaction product of:
(a) a compound of formula (A) as described above;
(b) a diol; and
(c) a diacid or anhydride.

As used herein the term "polymer" refers to a molecule made up of repeating monomer units wherein the molecule has a molecular weight of 7000 grams/mole or greater. As used herein the term "oligomer" refers to a molecule made up of repeating monomer units wherein the molecule has a molecular weight of less than 7000 grams/mole.

In another aspect, the invention provides curable compositions that may be useful, for example, as coatings. In one embodiment the curable compositions comprise a reactive diluent and a polyester polymer and/or oligomer of the invention. The compositions may be cured (i.e., polymerized) by exposure to electron beam (i.e., e-beam) radiation. In another embodiment, the curable composition comprises a reactive diluent, a photoinitiator, and a polyester polymer or oligomer of the invention. The compositions may be cured (i.e., polymerized) by exposure ultra-violet light.

DETAILED DESCRIPTION

The invention relates to di- and tri-functional carboxylic acid compounds that may be represented by formula (A). Compounds of formula (A) may be used, for example to prepare polyester oligomers and/or polyester polymers. In certain embodiments, the polyester oligomers and/or polymer have improved properties.

The di- and tri-functional compounds of the invention are represented by formula (A):

HOOC—Y—COOH   (A)

where:
—Y— is selected from the group consisting of:

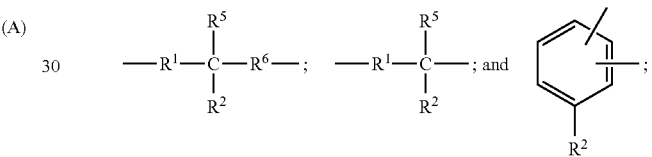

—$R^1$— is a divalent aliphatic organic group;
—$R^2$ is —X—C(=O)—$R^3$—C(=O)OH or —X—C(=O)—$R^4$;
—X— is —O— or —NH—;
—$R^3$— is a divalent organic group having at least one carbon-carbon double bond;
—$R^4$ is a monovalent organic group having at least one carbon-carbon double bond;
—$R^5$ is hydrogen or an alkyl group; and
—$R^6$— is a divalent aliphatic organic group.

Compounds of formula (A) may be prepared, for example, by reacting: (1) a hydroxy-functional dicarboxylic acid, an amine-functional dicarboxylic acid, a hydroxy-functional anhydride, or an amine-functional anhydride with (2) a dicarboxylic acid having at least one carbon-carbon double bond, an anhydride having at least on carbon-carbon double bond, or a mono-carboxylic acid having at least one carbon-carbon double bond. Mixtures and combinations of the foregoing may also be used.

Representative examples of hydroxy-functional dicarboxylic acids include malic acid (e.g., l-malic acid, d-malic acid, and d,l-malic acid), 3-hydroxy-3-methylglutaric acid, citramalic acid, and hydroxy aromatic dicarboxylic acids. A representative example of a hydroxy-functional anhydride is 3-hydroxyphthalic anhydride.

Representative examples of amine-functional dicarboxylic acids include glutamic acid and amino aromatic acids (e.g., 3-aminophthalic acid).

Representative dicarboxylic acids having at least one carbon-carbon double bond include itaconic acid, maleic acid, fumaric acid, mesaconic acid, citraconic acid. Representative anhydrides having at least one carbon-carbon double bond include itaconic anhydride, maleic anhydride and citraconic anhydride. Representative mono-carboxylic acids having at least one carbon-carbon double bond include methacrylic acid and its derivatives, crotonic acid and anhydride, unsaturated fatty acids such as oleic acid and linoleic acid.

In one embodiment of the invention, itaconic anhydride is reacted with malic acid to form the tri-functional carboxylic acid compounds of formula (A) shown below.

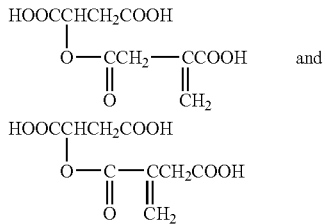

In another embodiment, itaconic anhydride is reacted with glutamic acid to form the tri-functional carboxylic acid compounds of formula (A) shown below.

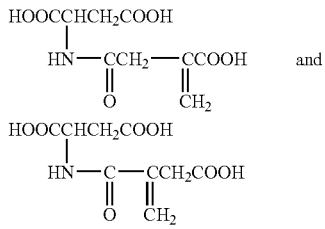

The di- and tri- carboxylic acid compounds of the invention may be used to prepare polyester oligomers and/or polyester polymers by reacting the compounds with: (1) dihydric alcohols, or (2) dihydric alcohols and dicarboxylic acids. Accordingly, in another embodiment, the invention provides polyester oligomers and polyester polymers made from the di- and/or tri- carboxylic acid compound of the invention. Polyester oligomers and polymers of the invention may be synthesized in several routes, as described below.

Route 1:

Step 1:

In the first synthetic route, a diol and a dicarboxylic acid (or anhydrides) are reacted in known fashion to form a polyester diol. The diol is added in excess with respect to the dicarboxylic acid or anhydride in a ratio of diol to dicarboxylic acid of 1.01:1 to 100:1 on amolar basis.

To enhance the reaction rate, a catalyst such as sulfuric acid, sulfonic acid, p-toluene sulfonic acid may be used, for example, in an amount ranging from about 0.05 to 5% weight. The reaction may be carried out at atmospheric pressure or, preferably, under reduced pressure of about 50 to about 500 mm Hg. In some embodiments, the reaction mixture is blanketed with an inert gas (e.g., carbon dioxide, nitrogen, or argon) to reduce side reactions with oxygen. The reaction is typically carried out at temperature ranging from about 60° C. to about 250° C. for a time ranging from about 15 minutes to about 24 hours.

In a specific embodiment, tetra(ethylene glycol) is reacted with succinic anhydride to form a polyester oligomer diol having the structure shown below.

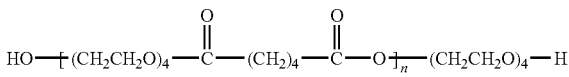

Step 2:

Separately, a hydroxy-functional or amine-functional diacid is reacted with an unsaturated anhydride and/or an unsaturated diacid or unsaturated monoacid to form an unsaturated triacid or unsaturated diacid compound of formula (A). The ratio of the unsaturated compound to the hydroxy-functional compound typically ranges from about 1.01:1 to 100:1 on a molar basis. To enhance the reaction rate, a catalyst such as tin powder, tin (II) chloride, tin (II) acetate, tin (II) oxide and lithium chloride may be used, for example, in an amount ranging from about 0.05% to 5% weight. In some embodiments, the carbon-carbon double bonds are protected by the addition of about 0.001 to about 1% weight of hydroquinone.

The reaction may be carried out at atmospheric pressure or, preferably, under reduced pressure of about 50 to about 500 mm Hg. In some embodiments, the reaction mixture is blanketed with an inert gas (e.g., carbon dioxide, nitrogen, or argon) to reduce side reactions with oxygen. The reaction is typically carried out at a temperature ranging from about 60° C. to about 170° C. for a time ranging from about 15 minutes to about 24 hours.

In one embodiment, malic acid is reacted with itaconic anhydride to form the compounds shown below.

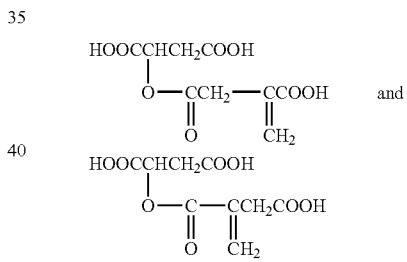

Step 3:

In the last step, the polyester oligomer diol or polyester polymer diol prepared in Step 1 and the triacid or diacid compounds of formula (A) that were prepared in Step 2 (and excess unsaturated compound) are reacted with each another. The ratio of the total mole number of carboxylic acid (i.e., —COOH) groups to the total mole number of hydroxyl (i.e., —OH) groups in the reaction mixture typically ranges from about 1.01:1 to 2:1. The reaction forms a polyester oligomer and/or polyester polymer having the structure shown below. The reaction may be carried out at atmospheric pressure, or more preferably, the reaction is carried out at a reduced pressure ranging from about 50 to about 500 mm Hg. In some embodiments, the reaction mixture is blanketed by an inert gas (e.g., carbon dioxide, nitrogen, or argon) to reduce side reactions with oxygen. The reaction is typically carried out at temperatures ranging from about 60° C. to about 170° C. for a time ranging from about 15 minutes to about 24 hours. Typically, the number average molecular weight ($\overline{M}_n$) of the resulting polyester oligomer and/or polyester polymer ranges from about 300 to about 30,000 grams/mole.

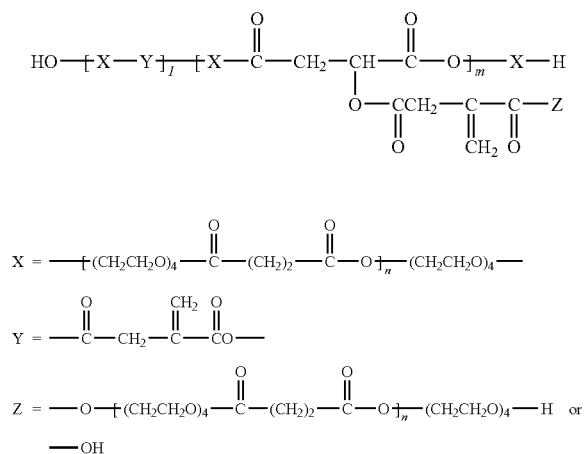

Route 2:

In the second synthetic route, a hydroxy-functional or amine-functional diacid is reacted with an unsaturated compound, for example, an unsaturated anhydride, an unsaturated diacid, or an unsaturated monoacid to form a diacid or triacid compound of formula (A). The ratio of unsaturated compound to the hydroxy-functional or amine-functional compound typically ranges from about 1.01:1 to 100:1 on a molar basis. In some embodiments, the carbon-carbon double bond is protected by the addition of about 0.001 to 1% weight of hydroquinone. To enhance the reaction rate, a catalyst, such as tin powder, tin (II) chloride, tin (II) acetate or tin (II) oxide, may be added in an amount ranging from about 0.05% to 5% weight. For example, malic acid may be reacted with itaconic anhydride as shown above.

To the mixture described above, a diol and a diacid or anhydride are added sequentially. The ratio of the total mole number of carboxylic acid (i.e., —COOH groups) to the total mole number of hydroxyl groups (i.e., —OH groups) in the reaction mixture typically ranges from about 1.01:1 to 2:1. The components are then reacted to form a polyester oligomer and/or polyester polymer of the invention. The reaction may be carried out at atmospheric pressure. More preferably, the reaction is carried out at a reduced pressure ranging from about 50 to about 500 mm Hg. In some embodiments, the reaction mixture is blanketed by an inert gas, including carbon dioxide, nitrogen, or argon to reduce side reactions with oxygen. The reaction is typically carried out at a temperature ranging from about 60° C. to about 170° C. for a time ranging from about 15 minutes to about 24 hours.

In a specific embodiment, tetra(ethylene) glycol and adipic acid are added to a compound of formula (A) sequentially to produce a polyester oligomer or polymer having a representative structure as shown below, where X, Y and Z are randomly distributed along the main chain of the oligomer or polymer.

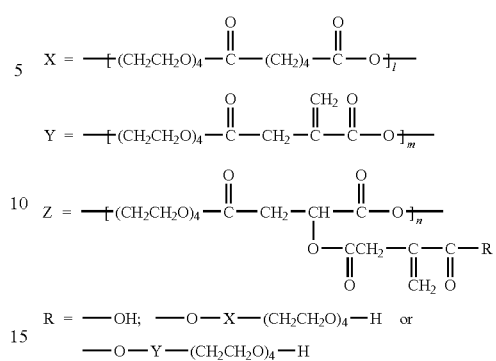

Route 3:

In the third synthetic route, a diol and a diacid (or anhydride) are reacted to form a polyester oligomer diol. For example, tetra(ethylene glycol) may be reacted with adipic anhydride to form a polyester oligomer diol having the structure shown below:

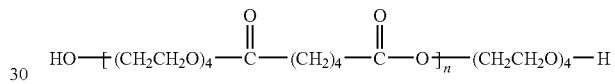

The reaction can be carried out at atmospheric pressure. More preferably, the reaction is carried out under reduced pressure ranging from about 50 to about 500 mm Hg. In some embodiments, the reaction mixture is blanketed by an inert gas, including nitrogen or argon. The reaction is typically carried out at the temperature ranging from about 60° C. to about 250° C. for a time ranging from about 15 minutes to about 24 hours. To enhance the reaction rate, a catalyst such as sulfuric acid, sulfonic acid, or p-toluene sulfonic acid may be added, for example, in an amount ranging from about 0.05 to 5% weight.

To the polyester oligomer diol, a hydroxy-functional or amine-functional diacid and an unsaturated anhydride or diacid or monoacid are then added. The ratio of the total mole number of carboxylic acid groups (—COOH) to the total mole number of hydroxyl groups (—OH) typically ranges from about 1.01:1 to about 2:1. The components are then reacted to form a polyester oligomer or polyester polymer. In some embodiments, the carbon-carbon double bond is protected by the addition of about 0.001 to 1% weight of hydroquinone. In a specific embodiment, malic acid and itaconic anhydride are added to the polyester oligomer diol to provide a polyester oligomer and/or polyester polymer having a representative structure as shown below:

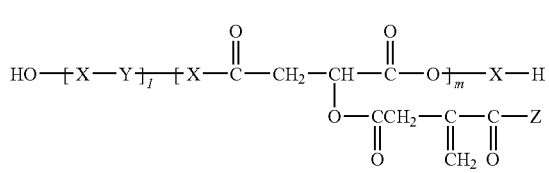

-continued

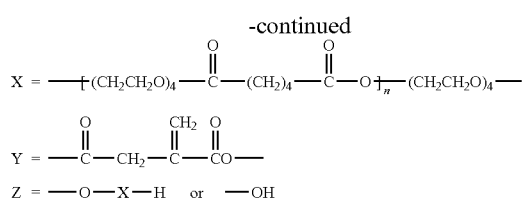

The polyester oligomer and/or polyester polymer typically has a number average molecular weight ($\overline{M}_n$) ranging from about 300 to about 30,000 grams/mole.

Materials used in preparing the polyester oligomers and polyester polymers of the invention are described in more detail below.

Dihydric Alcohol (Diol):

Polyester oligomer/polymer compositions the invention include at least one diol. As used herein the term "diol" refers to a molecule having two hydroxyl groups. Diols may be represented by the formula HO—R—OH, where —R— is a divalent organic group that optionally comprises O, P, S, N, and/or halogen.

Suitable diols include straight chain alkane diols, branched chain alkane diols and ether diols. Straight chain alkane diols are represented by formula (B) and ether diols are represented by formula (C).

Alkane Diols:

$$\text{HO}-(\text{CH}_2)_{n1}-\text{OH} \tag{B}$$

where n1 is 2 to 10.

Representative examples of straight chain alkane diols include 1,3-propanediol; 1,4-butanediol; 1,5-heptanediol; 1,6-hexanediol, 1,7-heptanediol, 1,8-octanediol, 1,9-nonanediol, and 1,10-decanediol.

Ether Diols:

$$\text{HO}-((\text{CH}_2)_{n2}-\text{O})_{n3}\text{H} \tag{C}$$

where n2 is 2 to 4; and n3 is 2 to 10.

Representative examples of ether diols include ethylene glycol (i.e., where n2=2 and n3=2), propylene glycols (i.e., where n2=3 and n3=2), and tetra(ethylene glycol) (i.e., where n2=2 and n3=4).

Branched chain hydrocarbon diols may also be used and include, for example, 1,2-propane diol (i.e., HOCH$_2$CH(CH$_3$)OH) and 1,3-butane diol (i.e., (HOCH$_2$CH$_2$CH(CH$_3$)OH).

Dicarboxylic acid or Anhydride:

Polyester oligomer and polymer compositions of the invention include a dicarboxylic acid or anhydride. The dicarboxylic acid or anhydride reacts with a diol to form ester linkages in the polyester oligomer or polymer. As used herein the term "anhydride" refers to a compound derived from an organic diacid by elimination of a molecule of water.

Suitable organic diacids may be represented by the general formula (D).

$$\text{HOOC}-\text{R}^7-\text{COOH} \tag{D}$$

where —R$^7$— is a divalent organic group including, for example, alkane (e.g., —(CH$_2$)$_{n4}$—;

where n4 is 2 to 8), alkene, a cycloaliphatic group, or an aromatic group.

Representative examples of alkane dicarboxylic acids include adipic acid, succinic acid, glutaric acid, and sebacic acid. Representative examples of unsaturated dicarboxylic acids include itaconic acid, maleic acid and fumaric acid. A representative example of a cycloaliphatic dicarboxylic acid is 1,2-cyclohexanedicarboxylic acid. Representative examples of aromatic dicarboxylic acids include phthalic acid and terephthalic acid.

Suitable anhydrides may be represented by the general formula (E).

where —R$^8$— is a divalent organic group including, for example, an alkane (e.g., —(CH$_2$)$_{n5}$—;

where n5 is 2 or 3), alkene, cycloaliphatic group or aromatic group.

Representative examples of anhydrides include succinic anhydride and glutaric anhydride. Representative examples of unsaturated dicarboxylic anhydrides include itaconic anhydride and maleic anhydride. Representative examples of cycloaliphatic dicarboxylic anhydrides include 1,2-cyclohexanedicarboxylic anhydrides. A representative example of an aromatic dicarboxylic anhydrides is phthalic anhydride.

In one embodiment, the invention provides curable compositions comprising a reactive diluent, a photoinitiator and a polyester polymer or oligomer of the invention. The compositions may be suitable, for example, as coatings.

Curable compositions of the invention may be polymerized by exposure to electron beam, or polymerization can be initiated by exposure to ultra-violet (UV) light when the composition comprises a photoinitiator. As used herein the term "photoinitiator" refers to a material that functions to initiate polymerization when exposed to UV radiation of a suitable wavelength. Representative examples of photoinitiators include 2,2-dimethoxy-2-phenylacetophenone, benzophenone, benzoin alkyl ether.

Reactive diluents are materials that include one or more double bonds that can be initiated by the radicals generated by the photoinitiator. Representative examples of reactive diluents include 2-(2-ethoxyethoxy)ethyl acrylate, isodedcyl acrylate, ethoxylated neopentyl glycol diacrylate, polyethyleneglycol 400 diacrylate, tetra(ethylene glycol) diacrylate, tri(propylene glycol) diacrylate trimethylolpropane triacrylate, propoxylated glyceryl triacrylate, and ethoxylated pentaerythritol tetraacrylate.

The invention will be further illustrated below with reference to the following Examples, which are intended to aid in the understanding of the present invention, but which are not to be construed as a limitation thereof.

EXAMPLES

| Material List | |
|---|---|
| Chemical Name | Source |
| d,l-malic acid | Sigma Aldrich Cat No. 240176 |
| SnCl$_2$ (Tin(II) chloride) | Sigma Aldrich Cat No. 208256 |
| hydroquinone | Sigma Aldrich Cat No. 240125 |

-continued

Material List

| Chemical Name | Source |
|---|---|
| itaconic anhydride | Sigma Aldrich Cat No. 259926 |
| adipic acid | Sigma Aldrich Cat No. A5252 |
| tetra(ethylene glycol) | Sigma Aldrich Cat No. 110175 |
| succinic anhydride | Sigma Aldrich Cat No. 239690 |
| 2,2-dimethoxy-2-phenylacetophenone | Sigma Aldrich Cat No. 196118 |
| trimethylolpropane triacrylate (TMPTA) | Sigma Aldrich Cat No. 246808 |

Example 1

Route 2

Synthesis of Polyester Oligomer 0.537 g of d, l-malic acid, 0.0396 g of $SnCl_2$ and 0.0023 g of hydroquinone were added to 2.241 g of molten itaconic anhydride. The stirred mixture was heated under nitrogen at 90° C. for 1 hrs. Then 7.77 g of tetra(ethylene glycol) and 2.920 g of adipic acid were added to the above mixture under nitrogen sequentially. Then the temperature was raised to 95° C. and the mixture was stirred for 7 hours. The resulting reaction mixture was cooled to room temperature and was discharged. The product was light yellow viscous gel. The number average molecular weight of the product was determined to be 2170 grams/mole from GPC (polystyrene as standard on a Water 2690 apparatus; columns, Styragel® HR 0.5 and Styragel® HR 2; eluent, THF; flow rate, 0.3 mL/min; column temperature, 35° C.).

Example 2

Route 1

Synthesis of Polyester Oligomer

Step (1):

0.134 g of d, l-malic acid was added to 0.672 g of itaconic anhydride and 0.001 g of hydroquinone under nitrogen at 120° C. The reaction mixture was stirred for 4.5 hours and D, L-malic acid was completely reacted with itaconic anhydride (HPLC monitoring using Shimadzu LC-10AT, column, Aminex® HPX87H; eluent 0.01 N sulfuric acid solution; flow rate 0.5 mL/min; column temperature 60° C.).

Step (2):

2.918 g of tetra(ethylene glycol) and 1 g of succinic anhydride were mixed at 120° C. The reaction mixture was stirred for 4.5 hours.

Step (3):

The compounds prepared in step (1) and step (2) were combined under a blanket of nitrogen. After addition, the stirred reaction mixture was heated to 95° C. for 15.5 hours. Subsequently, the reaction mixture was cooled to room temperature, yielding a light yellow viscous gel.

The number average molecular weight of the gel was determined to be 1650 grams/mole from GPC (polystyrene as standard on a Water 2690 apparatus; columns, Styragel® HR 0.5 and Styragel® HR 2; eluent, THF; flow rate, 0.3 mL/min; column temperature, 35° C.).

Example 3

UV Curing of Compound of Example 1

0.060 g of 2,2-dimethoxy-2-phenylacetophenone photoinitiator was dissolved in 0.616 g of trimethylolpropane triacrylate (TMPTA) to provide a photoinitiator solution. 1.16 g of the product of Example 1 was added to the photoinitiator solution and was stirred until the mixture was uniform. A thin film of the mixture was applied to paperboard and the resulting film was cured under a 200 W/inch ultraviolet light in a nitrogen purged environment (cured under a portable 2" UV curing system commercially available under the trade designation "CON-TROL-CURE" from UV Process Supply, Inc.). The cured film was tack-free, transparent, and rigid.

Other embodiments of the invention will be apparent to those skilled in the art upon consideration of this specification or from practice of the invention disclosed herein. Various modifications and changes to the principles and embodiments described herein may be made by one skilled in the art without departing from the true scope and spirit of the invention which is indicated by the following claims. All patents, patent documents, and publications cited herein are hereby incorporated by reference as if individually incorporated.

What is claimed is:

1. A composition of matter comprising:

a compound of formula (A):

$$\text{HOOC—Y—COOH} \qquad (A)$$

wherein —Y— is

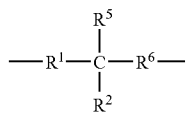

—$R^1$— is a divalent aliphatic organic group;
—$R^2$— is —X—C(=O)—$R^3$—C(=O)OH or —X—C(=O)—$R^4$;
—X— is —O— or —NH—;
—$R^3$— is a divalent organic group having at least one carbon-carbon double bond;
—$R^4$ is a monovalent organic group having at least one carbon-carbon double bond;
—$R^5$ is hydrogen or an alkyl group; and
—$R^6$— is a divalent aliphatic organic group.

2. A composition of matter comprising a compound selected from the group consisting of:

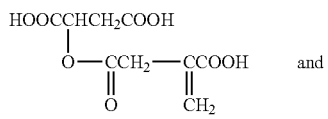 and

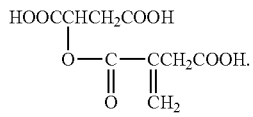

3. A composition of matter comprising a compound selected from the group consisting of:

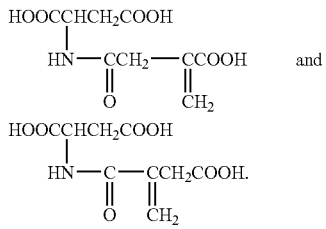

and

4. A composition of matter comprising:
a polyester oligomer or polyester polymer comprising the reaction product of:
(a) a compound of formula (A):

$$HOOC-Y-COOH \quad (A)$$

where —Y— is selected from the group consisting of:

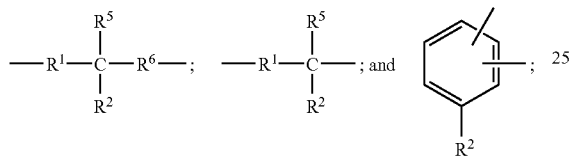

and where:
—$R^1$— is a divalent aliphatic organic group;
—$R^2$ is —X—C(=O)—$R^3$—C(=O)OH or —X—C(=O)—$R^4$;
—X— is —O— or —NH—;
—$R^3$— is a divalent organic group having at least one carbon-carbon double bond;
—$R^4$ is a monovalent organic group having at least one carbon-carbon double bond;
—$R^5$ is hydrogen or an alkyl group; and
—$R^6$— is a divalent aliphatic organic group;
(b) a diol; and
(c) a diacid or anhydride.

5. The composition of matter of claim 4, wherein the diol is an alkane diol having the formula:

$$HO-(CH_2)_{n1}-OH$$

where n1 is 2 to 10.

6. The composition of matter of claim 5, wherein the diol is selected from the group consisting of 1,3-propanediol; 1,4-butanediol; 1,5-heptanediol; 1,6-hexanediol, 1,7-heptanediol, 1,8-octanediol, 1,9-nonanediol, and 1,10-decanediol.

7. The composition of matter of claim 4, wherein the diol is an ether diol having the formula:

$$HO-((CH_2)_{n2}-O)_{n3}H$$

where n2 is 2 to 4; and
n3 is 2 to 10.

8. The composition of matter of claim 7, wherein the diol is selected from the group consisting of ethylene glycol, propylene glycol, and tetra(ethylene glycol).

9. The composition of matter of claim 4, wherein the diol is 1,2-propane diol or 1,3-butane diol.

10. The composition of matter of claim 4, wherein the diacid has the formula:

$$HOOC-R^7-COOH$$

where —$R^7$— is a divalent organic group selected from the group consisting of alkanes, alkenes, cycloaliphatic groups, and aromatic groups.

11. The composition of matter of claim 10, where the diacid is selected from the group consisting of adipic acid, succinic acid, glutaric acid, sebacic acid, itaconic acid, maleic acid, fumaric acid, 1,2-cyclohexanedicarboxylic acid, phthalic acid and terephthalic acid.

12. The composition of matter of claim 4, wherein the anhydride has the formula

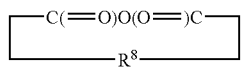

where —$R^8$— is a divalent organic group selected from the group consisting of an alkanes, alkenes, a cycloaliphatic group and an aromatic group.

13. The composition of matter of claim 12, wherein the anhydride is selected from the group consisting of succinic anhydride, glutaric anhydride, itaconic anhydride, maleic anhydride, 1,2-cyclohexanedicarboxylic anhydrides and phthalic anhydride.

14. A curable composition of matter comprising:
a reactive diluent; and
a composition of matter according to claim 4.

15. The composition of claim 14, wherein the composition has been cured by electron beam.

16. The curable composition of claim 14, wherein the reactive diluent is selected from the group consisting of 2-(2-ethoxyethoxy)ethyl acrylate, isodedcyl acrylate, ethoxylated neopentyl glycol diacrylate, polyethyleneglycol diacrylate, tetra(ethylene glycol) diacrylate, tri(propylene glycol) diacrylate, trimethylolpropane triacrylate, propoxylated glyceryl triacrylate, and ethoxylated pentaerythritol tetraacrylate.

17. A curable composition of matter comprising:
a reactive diluent;
a photoinitiator; and
a composition of matter according to claim 4.

18. The curable composition of claim 17, wherein the photoinitiator is selected from the group consisting of 2,2-dimethoxy-2-phenylacetophenone, benzophenone, and benzoin alkyl ether.

19. The curable composition of claim 17, wherein the reactive diluent is selected from the group consisting of 2-(2-ethoxyethoxy)ethyl acrylate, isodedcyl acrylate, ethoxylated neopentyl glycol diacrylate, polyethyleneglycol diacrylate, tetra(ethylene glycol) diacrylate, tri(propylene glycol) diacrylate, trimethylolpropane triacrylate, propoxylated glyceryl triacrylate, and ethoxylated pentaerythritol tetraacrylate.

20. The curable composition of claim 17, wherein the composition has been cured by exposure to ultraviolet light.

* * * * *